United States Patent [19]

Masinter

[11] Patent Number: 4,938,776
[45] Date of Patent: Jul. 3, 1990

[54] INTEGRATED ANKLE AND FOOT PROSTHETIC SYSTEM

[76] Inventor: Robert A. Masinter, 408 Laurel Ave., Menlo Park, Calif. 94025

[21] Appl. No.: 350,788

[22] Filed: May 12, 1989

[51] Int. Cl.$^5$ ............................................. A61F 2/66
[52] U.S. Cl. ...................................... 623/49; 623/55
[58] Field of Search ................................... 623/47–56, 623/49, 50, 53, 55

[56] References Cited

U.S. PATENT DOCUMENTS

| | | | |
|---|---|---|---|
| 817,340 | 4/1906 | Rosenkranz | 623/49 |
| 3,707,731 | 1/1973 | Morgan | 623/49 |
| 4,180,872 | 1/1980 | Chaikm | 623/55 |
| 4,547,913 | 10/1985 | Phillips | 623/27 |
| 4,645,509 | 2/1987 | Poggi | 623/55 |
| 4,792,340 | 12/1988 | Aulie et al. | 623/49 |

FOREIGN PATENT DOCUMENTS

| | | | |
|---|---|---|---|
| 0308671 | 10/1918 | Fed. Rep. of Germany | 623/55 |
| 8800815 | 2/1988 | PCT Int'l Appl. | 623/53 |

Primary Examiner—Randall L. Green
Assistant Examiner—David H. Willse
Attorney, Agent, or Firm—Karl W. Flocks

[57] ABSTRACT

Integrated prosthetic ankle and foot structure comprising an ankle portion of larger longitudinal dimension and smaller lateral dimension with a flexible and resilient ankle portion capable of both compression and expansion and a foot structure including a foot plate with a relatively thicker heel portion and a thinner grooved or kerfed toe part.

10 Claims, 3 Drawing Sheets

U.S. Patent Jul. 3, 1990 4,938,776
FIG. 1
FIG. 3
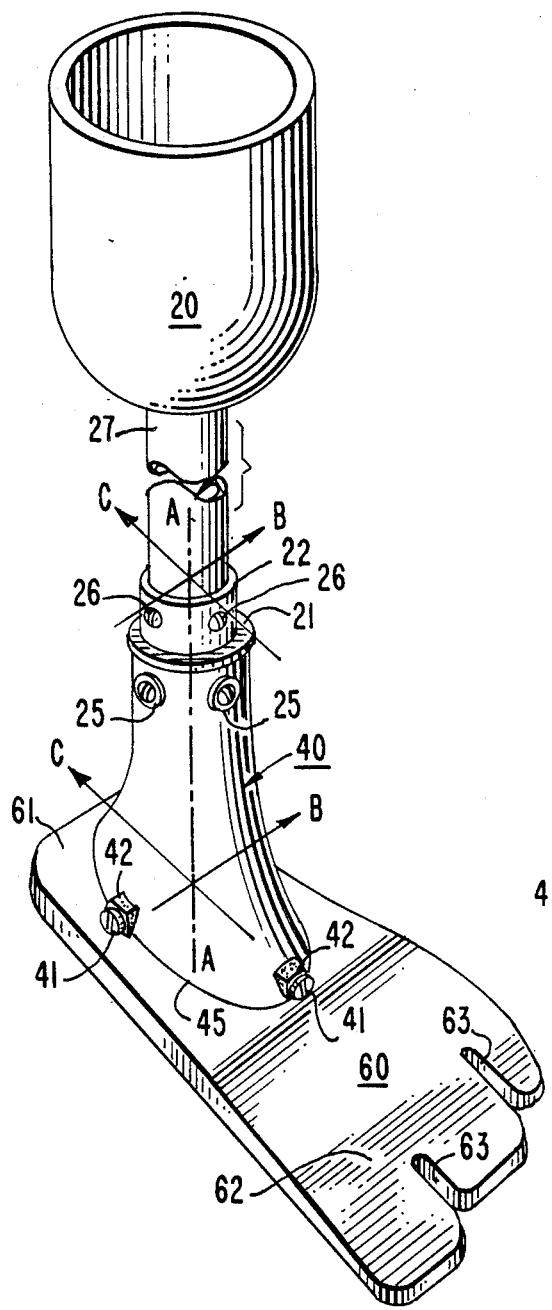
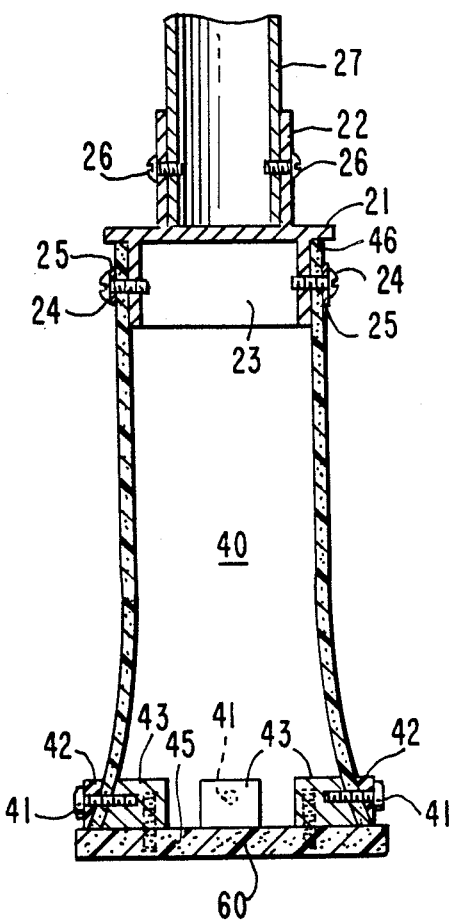

INTEGRATED ANKLE AND FOOT PROSTHETIC SYSTEM

This invention relates to a prosthetic device in the form of an integrated artificial ankle and foot to replace the ankle and foot of one who has lost these natural body members in an accident or who had these body members removed because of sickness or disease or for other significant reasons. More particularly, the invention relates to an artificial, integrated ankle and foot assembly which facilitates and permits a lower extremity amputee to walk more naturally on surfaces of variable slope than is currently possible with existing prosthetic components.

BACKGROUND

In the recent past, prior to the instant invention, "energy-storing" prosthetic devices built for and marketed in this field have taken the simple form illustrated in FIG. 7 of the drawings wherein a strong and flexible graphite-composite plate is shaped to provide an ankle portion "b", and a toe portion "c", and is affixed to a smaller plate to provide a heel portion "d".

The energy-storing capacity of the device, illustrated in FIG. 7, is intrinsic to the graphite-composite material utilized in its construction. However, the simple design of the unit is found to be inadequate in its inability to approximate the range of motion possible in a human ankle.

More multi-directional flexibility in the ankle-portion of the device coupled with a more stable basal portion of the device is needed to fulfill the requirements of an active user.

Although ball and socket joints may be suggested for an artificial ankle structure, more and complicated elements may have to be incorporated in an attempt to effect the desired control for an active user or even for a relatively sedentary user.

OBJECTS OF THE INVENTION

It is an object of the instant invention to provide a novel integrated ankle and foot structure with superior functional capabilities for a lower extremity amputee. This structure can be connected to a conventional pylon and thereby conventionally affixed to either a socket for below knee amputees or an artificial knee for above knee amputees.

Another object is to provide a novel integrated ankle and foot structure with inherently operative front to back or anterior and posterior elasticity and flexibility and with inherently operative medial-lateral or left to right elasticity and stability of such characteristics as to accomodate both active and sedentary users in corresponding activity.

A further object is to provide a novel integrated ankle and foot structure wherein the ankle portion is simply fabricated from sheets of woven carbon fiber subsequently impregnated with epoxy resin molded in a shape taking the general form of a somewhat modified frustum of a cone having an elliptical base.

Still another object is to provide a novel integrated ankle and foot wherein the foot portion is simply fabricated from sheets of woven carbon fiber subsequently impregnated with epoxy resin. This naturally-shaped foot plate imparts basal stability to the total structure and also incorporates a taper in the thickness generally from the heel end to the grooved or kerfed toe end.

BRIEF DESCRIPTION OF DRAWINGS

FIG. 1 is a view in perspective of the combined ankle and foot structure;

FIG. 3 is a view in vertical cross-section taken in a laterally oriented plane through the ankle axis A—A and looking in the direction of the arrows C, C of FIG. 1;

Referring to FIGS. 1-6 of the Drawings, the two primary components of the artificial combined ankle and foot assembly are the element 40 herein referred to as the ankle-cone, and the element 60 herein referred to as the foot plate The stainless steel or titanium junction sleeve 21 is utilized to connect the ankle-cone to the pylon 27 which, in turn, is joined to the lower portion of the socket 20.

Figure 2:
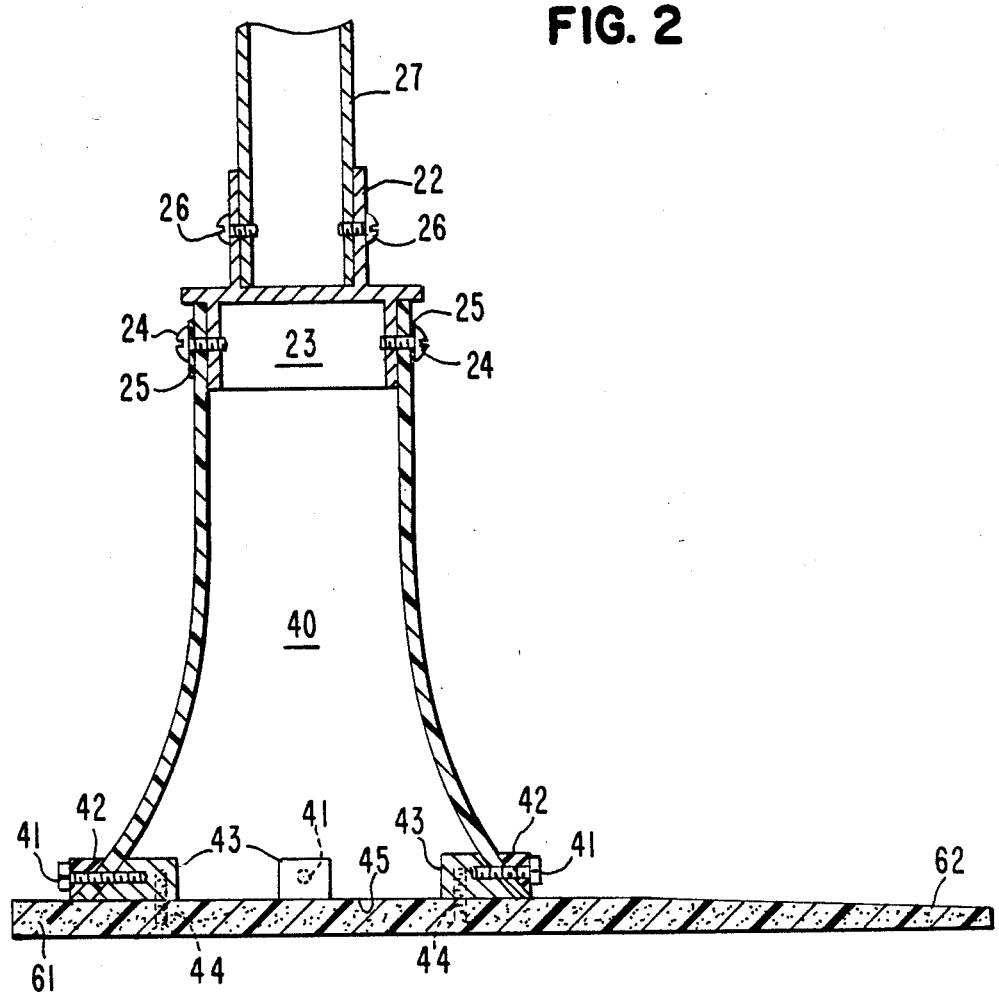
FIG. 2 is a view in longitudinally oriented vertical cross-section taken in a plane through the ankle axis A—A and looking in the direction of the arrows B, B of FIG. 1.

Formed integrally with the junction sleeve 21 is the upwardly extending sleeve portion 22 which is secured to the aluminum pylon 27 by the machine bolt 26 or by a clamping system such as is available by "Otto Bock".

Extending downwardly from the junction sleeve, element 21 is the sleeve portion 23 which is secured to the upper end of the ankle-cone element 40 by machine bolts 24 extending through rubber washers 25. A clamping system as described above may be substituted as a method for attachment.

Figure 5:
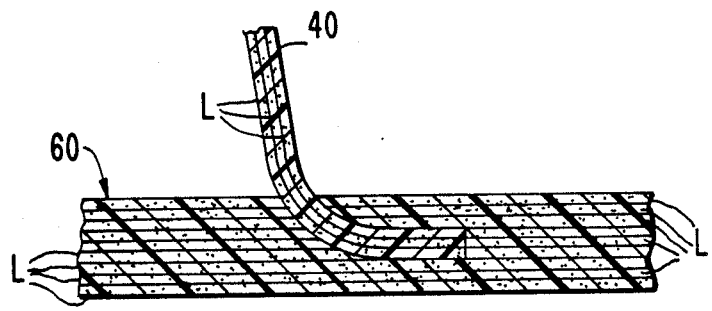
FIG. 5 is a fragmentary vertical cross-section of a modified form illustrating assembly of the ankle to the foot.
Figure 6:
FIG. 6 is a side elevation of the foot.

The lower end or base of the ankle-cone 40 is assembled with the foot plate 60 either as illustrated in FIG. 2 for prototype testing or permanently, as illustrated in FIG. 5. In FIG. 2 the bolts 41 extend through the rubber washers 42 and into the stainless steel wedges 43 which match and engage portions of the lower interior and exterior surfaces of the ankle-cone 40. The machine bolts 44 connect the foot plate 60 to the interior-situated stainless steel wedges 43 to effect the connection between the foot plate 60 and the ankle-cone 40. FIG. 5 shows how the laminated ankle-cone 40 may be assembled with the laminae of the foot plate 60 so that after the curing process involving the setting of the thermosetting epoxy resin, with which each lamina L is impregnated, an integral ankle-cone and foot plate structure results.

Referring more particularly to the ankle-cone structure 40 as illustrated in FIGS. 1, 2, 3, 4, and 5, it will be observed that the base 45 is elliptical and the upper extremity 46 is circular. The ankle-cone 40 is so constructed that it has a quality of being both operatively flexible and operatively resilient. It can flex or strain when forced or stressed by the User and, because of memory inherent in its carbon-composite construction, it resiliently returns to its original unstressed or unstrained shape or form when the user discontinues the force or stress. In this way the novel ankle-cone 40 inherently provides front to back and side to side (or anterior-posterior and medial-lateral) elasticity and flexibility.

These qualities are enhanced by the illustrated departure from a geometrically true frustum of a cone in that the ankle-cone 40 has an elliptical base with a major axis running from front to back and a minor axis running from side to side. In addition the ankle-cone structure departs from a true frustum of a cone in that the side walls which extend vertically upwardly are concave. The ankle-cone 40 enables the wearer to transfer anterior, posterior, medial, or lateral directed flexion to the foot plate. For example, when the user flexes forward, the anterior portion of the ankle-cone compresses and the posterior portion of the ankle-cone expands. In a like manner, ankle-cone will compress and expand to accomodate any directional flexing by the wearer. The elliptical configuration of the ankle-cone base contributes to and enables dynamic anterior-posterior flexion and at the same time, allows controlled medial-lateral movement.

Figure 4:
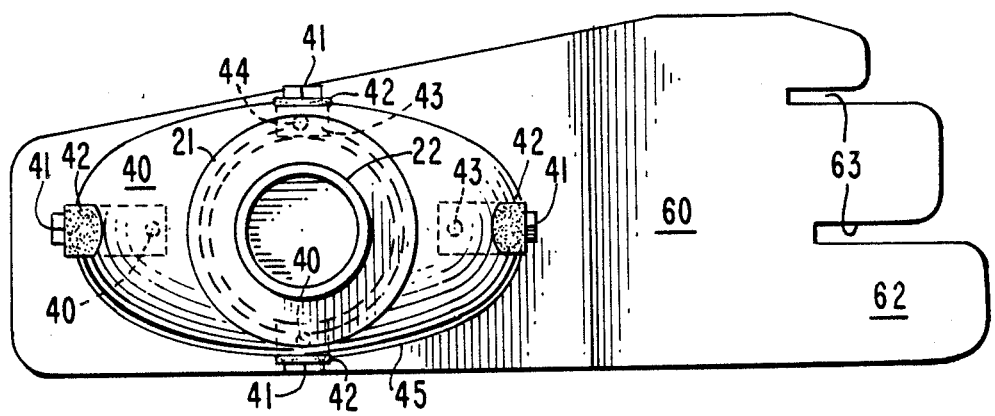
FIG. 4 is a plan view of the combined ankle and foot structure.
Figure 7:
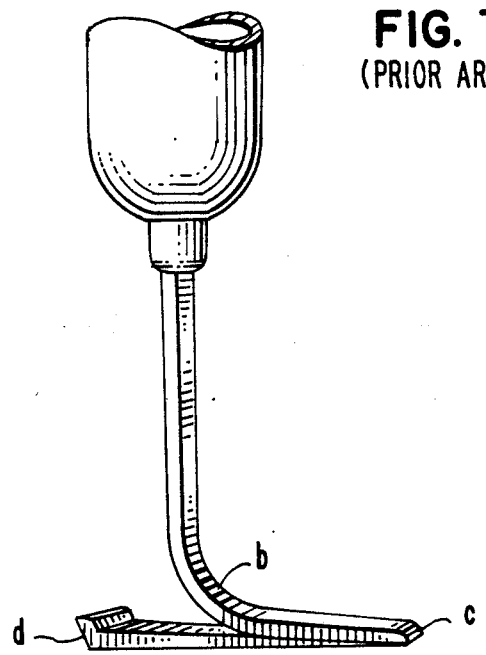
FIG. 7 is a view in perspective taken from the side of a prior art structure sold by Flex Foot, Inc., of California.

The foot plate 60, like the ankle-cone 40 is made up of laminated, woven sheets of carbon fiber, subsequently impregnated with an epoxy resin. The foot plate 60 tapers slightly from a place intermediate its rear 61 and toe portion 62 toward the toe portion 62. This taper provides for greater flexibility in the toe region. Grooves or kerfs 63 are cut into the toe portion 62 parallel to the longitudinal axis of the foot plate in order to create individually flexing subportions which will act to follow the manner of toes on a human foot. The outline of the foot plate 60, as illustrated in FIG. 4, is patterned after the outline of a human foot and serves to assist in affording greater lateral and basal stability, particularly as compared with the narrow keeled units currently available, as will be seen, for example, in FIG. 7. Thus, it will be understood that the foot plate 60 specially cooperates with the ankle-cone 40 in a novel manner to produce an advantageous result.

The epoxy-impregnated carbon fiber material of the ankle-cone 40 and foot plate 60 endows these elements with an energy storing capability. This property is advantageously utilized during the loading and unloading of the ankle-cone and foot plate components of the structure with force exerted by the weight of the user. During activity, this quality of the impregnated carbon fiber material provides a springy, lifelike gait to the user.

Integrating this material into the design of the invention described will enable the user to walk more naturally up and down hills and along the sides of hills. Advantageously the user accomplishes these natural functions with the utilization of the inherent flexion of the ankle-cone 40 and the flexion of the forward portion 62 of the foot plate 60 which is both tapered and grooved or kerfed. Additionally, the user will be able to wear this integrated system without a shoe, if desired, owing to the ability of the cone to absorb any angle of flexion directed to it. The integrated foot and ankle prosthetic system can be covered with conventional closed-cell foam to fashion a sightly cosmesis. If the internal parts of the system are all carbon graphite or titanium or aluminum, the unit can also be used for swimming.

The novel integrated foot and ankle structure has been described with respect to preferred forms illustrated in the drawings; however, it will be apparent to those who follow the above specifications and drawings that modifications may be made and equivalent elements may be substituted without departing from the spirit of the invention.

What is claimed is:

1. Integrated ankle and foot structure wherein the ankle portion is generally in the form of a modified frustrum of a cone with a generally elliptical base and a top of geometrical outline having a horizontal sectional area less then that of the elliptical base, wherein this ankle portion cone has a larger longitudinal dimension at its horizontal base than its lateral dimension, wherein this ankle cone is both flexible and resilient and capable of both compression and expansion at the forward, rearward, and lateral sides of the ankle and combinations thereof, wherein this flexible yet resilient ankle cone is affixed toward the rear of an elongate basal plate constructed from flexible and resilient material as aforesaid and generally in the shape of a flattened human foot, wherein a junction member extends from the top of the ankle cone and is adapted to be affixed to a conventional pylon.

2. Integrated ankle and foot structure wherein the ankle portion has a larger longitudinal dimension at its generally horizontal base than its lateral dimension, the forward part of the ankle portion being both flexible and resilient, capable of both compression and expansion, the rearward part of the ankle portion being both flexible and resilient and capable of both compression and expansion, a first side part of the ankle portion laterally spaced from a second side part, said first and second side parts each being both flexible and resilient and capable of both compression and expansion, said structure being so arranged that when said forward part is compressed the rearward part expands and when the rearward part is compressed then the forward part expands and when one side part is compressed then the other side part expands, and wherein the ankle portion is generally in the form of a modified frustrum of a cone with a generally elliptical base and a generally circular top.

3. Integrated ankle and foot structure in accordance with claim 2 wherein the front, rear, first side, and second side of said modified cone are concave in vertical section.

4. Integrated ankle and foot structure in accordance with claim 1, wherein said basal foot plate includes a heel part and a grooved or kerfed toe part and wherein the toe part is thinner than said heel part and wherein the lateral dimension of said foot plate is slightly greater than the lateral space between the side parts of said ankle portion at the base of the ankle portion, where it is affixed to the foot plate.

5. Integrated ankle and foot structure as set forth in claim 2, wherein the upper end of said ankle portion is fastened to said junction member which in turn is fastened to an upwardly extending pylon.

6. Integrated ankle and foot structure in accordance with claim 4, wherein the ankle portion is molded of laid up epoxy-resin impregnated, woven, carbon fiber belts.

7. Integrated ankle and foot structure in accordance with claim 4, wherein the basal foot plate is molded of laid up epoxy resin impregnated, woven, carbon fiber sheets.

8. Integrated ankle and foot structure in accordance with claim 6, wherein said belts extend into and between laid up epoxy resin impregnated woven carbon fiber sheets or belts of the foot plate which, when so assembled and molded, form the assembly of the ankle portion to said foot plate.

9. The structure recited in claim 5, wherein said junction member comprises a generally horizontal central portion having an outer margin shoulder formation, a sleeve portion extending upwardly from said central portion and a sleeve portion extending downwardly from said central portion, said upwardly extending portion adapted to receive said pylon and said downwardly extending portion adapted to be encompassed by the upper end of said ankle portion which will abut said outer margin shoulder formation.

10. The structure recited in claim 1, wherein said junction member comprises a generally horizontal central portion having an outer margin shoulder formation, a sleeve portion extending upwardly from said central portion, a sleeve portion extending downwardly from said central portion, said upwardly extending portion adapted to receive said pylon and said downwardly extending portion adapted to be encompassed by the upper end of said ankle cone which abuts the outer margin shoulder formation.

* * * * *